United States Patent
Whateley (12) 
(10) Patent No.: US 6,766,071 B2
(45) Date of Patent: Jul. 20, 2004

(54) DEVICE AND METHOD FOR THE MEASUREMENT OF THE HEAT OF A REACTION

(75) Inventor: John Gerard Whateley, Whitchurch (GB)

(73) Assignee: Amersham Biosciences UK Ltd., Amersham (GB)

(*) Notice: Subject to any disclaimer, the term of this patent is extended or adjusted under 35 U.S.C. 154(b) by 69 days.

(21) Appl. No.: 10/286,022

(22) Filed: Nov. 1, 2002

(65) Prior Publication Data

US 2003/0095735 A1 May 22, 2003

(30) Foreign Application Priority Data

Nov. 16, 2001 (GB) .............................................. 0127475

(51) Int. Cl.[7] .......................... G02B 6/00; G01N 33/551
(52) U.S. Cl. ........................ 385/12; 436/524; 385/147; 250/227.14
(58) Field of Search ................................ 385/12–13.16, 385/147; 436/524; 250/227.19, 227.23, 227.27, 227.14; 356/51, 317, 318

(56) References Cited

U.S. PATENT DOCUMENTS 5,578,499 A * 11/1996 Ismail .......................... 436/524

* cited by examiner

*Primary Examiner*—Akm Enayet Ullah
(74) *Attorney, Agent, or Firm*—Royal N. Ronning, Jr.; Yonggang Ji; Stephen G. Ryan (57) ABSTRACT

Disclosed is an apparatus for use in the measurement of the heat generated in a chemical or biochemical reaction, by detecting and measuring a change in the conformation of a polymer transducer responsive to a heat change, the transducer being bound to the surface of the waveguides of an interferometer. The conformational change is detected by optical means and is compared with a control. The polymer transducer may be selected from an organic polymer or a biological macromolecule.

10 Claims, 6 Drawing Sheets

Fig. 1

Schematic of Sensor Region

DEVICE AND METHOD FOR THE MEASUREMENT OF THE HEAT OF A REACTION

This invention relates to an apparatus and a method for the measurement of the heat generated in a chemical or biochemical reaction, by detecting and measuring a change in the conformation of a polymer transducer responsive to a heat change and being bound to the surface of a waveguide of an interferometer. The conformational change is detected by optical means and is compared with a control.

Assays involving biochemical reactions have hitherto generally required the use of a labelled reagent, for example a radioactive label or a fluorescent probe. Fluorescent labels have the disadvantage that they are generally bulky molecules that can change the structure and biological activity of the biochemical reagent that they are used to label. Radioactively labelling a molecule has the advantage that the molecule usually remains in its "native" conformation. However, there are other drawbacks to this method, including: i) the radioactive decomposition of the molecule; ii) the radioactive label can generally only be inserted synthetically into the molecule; iii) if the radioactive label is added as part of a labelling reagent, it has the same disadvantage as fluorescent probes; and iv) handling and disposal of radioactive material. In those cases where no labelled reagent is used, it is usually necessary to develop methods for the separation of the reactants from products, prior to analysis of the amounts of reactant consumed, or product formed.

Ideally, a method that would use "native" reagents and could monitor the progress of biochemical processes would be more suitable for the identification of enzyme inhibitors, antagonists, etc.

Essentially all biochemical and chemical reactions are associated with a change in enthalpy, and either take up or give off heat to the environment during the reaction. Since these reactions are typically performed in aqueous or organic solvent, the solvent changes temperature during the reaction. If this temperature change can be measured, then the rate and extent of the reaction can be measured directly. The ability to measure enthalpy changes through temperature changes in the solvent would obviate the need for labelling reagents, or the isolation of substrates or products to measure the extent of the reaction.

Microcalorimeters are useful for analytical measurements of biological or chemical reactions but are not currently useful in high throughput screening (HTS) applications for pharmaceutical screening purposes. Currently, microcalorimeters are capable of measuring enthalpy changes of 1 $\mu$J or greater and usually require test volumes of 1–1.5 ml. Most biochemical reactions have enthalpy changes of the order of magnitude ~100 kJ/mol. In a typical biochemical assay volume of 100 $\mu$l and a substrate concentration of the order of 1 nanomolar, the maximum amount of heat released by a sample and the corresponding temperature increase (assuming no heat is lost to the environment), is of the order $10^{-8°}$ K. Thus, the temperature change associated with such assays is below the detection limits of current microcalorimeters.

Integrated optical Mach-Zehnder interferometers (IO-MZI) have been employed as sensors for the detection and measurement of biological and biochemical interactions.

For example, Brosinger et al (Sensors and Actuators, (1997), B 44, 350–355) describe an IO-MZI for use as an affinity sensor in which one branch of the device was coated with antigen and a phase change caused by specific interactions of immunoglobulins with the antigenic surface.

The present invention relates to an improved method and an apparatus for the measurement of heat changes in a chemical or biochemical reaction that increases the sensitivity of measurement compared with conventional methods, while concurrently reducing assay volumes and the quantity of reagents compared with those conventionally used in such assays. In addition, as discussed by Brosinger et al (loc cit), a major disadvantage of affinity biosensors is the difficulty in distinguishing unwanted non-specific reactions of protein-containing solutions with the sensor surface. The present invention overcomes this problem by preventing the sensor surface making contact with the sample.

In a first aspect of the invention there is provided a method for measuring a heat change in a reaction to be studied, the method comprising:

i) contacting a surface of a waveguide with a liquid including one or more components of said reaction to be studied said surface having a transducer responsive to a heat change in said reaction and being coated on and bound thereto;

ii) directing a beam of electromagnetic radiation through said waveguide in the absence and in the presence of an initiator of said reaction to produce a fringe pattern including a plurality of spaced light bands whose positions shift in response to changes in the heat of said reaction;

wherein the positional shifts of said light bands in said fringe pattern measured in the absence and in the presence of said initiator are used to calculate the heat change in said reaction.

In a second aspect of the invention, there is provided a method for measuring a heat change in a reaction to be studied, the method comprising:

i) contacting at least a portion of the surface of a sample waveguide and of a reference waveguide of an interferometer with a liquid including one or more components of said reaction, each said surface having a transducer responsive to a heat change in said reaction and being coated on and bound thereto;

ii) directing a beam of electromagnetic radiation simultaneously through said sample waveguide and said reference waveguide such that a fringe pattern is produced said fringe pattern including a plurality of spaced light bands whose positions shift in response to changes in the heat of said reaction;

iii) adding to said one or more components in contact with said sample waveguide an initiator of said reaction; and iv) determining the heat change in said reaction by measuring the positional shifts of said light bands in said fringe pattern.

In a third aspect of the invention, there is provided an interferometric system, said system comprising a sample waveguide, a reference waveguide, and an outgoing waveguide;

wherein said sample and reference waveguides are formed of a material exhibiting an index of refraction, said sample and reference waveguides being joined at a first junction to an inlet waveguide and at a second junction to the outgoing waveguide such that electromagnetic radiation is allowed to pass simultaneously in parallel through said sample and reference waveguides;

characterised in that each of said sample waveguide and said reference waveguide comprises a surface that is coated with a transducer responsive to a heat change in a reaction and is bound thereto.

In a fourth aspect of the invention, there is provided use of an organic polymer or a biological macromolecule as a transducer for the measurement of a heat change generated in a chemical or a biochemical reaction to be studied.

The present invention therefore relates to the indirect determination of the heat of a reaction to be studied, suitably a biological or biochemical reaction, by monitoring a change in the conformation of molecules of a transducer that is in close proximity with a liquid reaction mixture, the transducer being coated onto and bound to the surface of the sample and reference waveguides of an interferometer. The change in conformation of the transducer molecules results in a change in the refractive index of the transducer, thereby producing a phase change in the electromagnetic radiation being transmitted through the waveguide.

Suitably, the interferometer is a Mach-Zehnder interferometer.

Suitably, the transducer is a material that is responsive to a heat change in the sample of the reaction to be studied, when the sample is in close proximity, or is in contact with, the transducer. The transducer is suitably a polymer, including an organic polymer or a biological macromolecule, which may be coated onto the surface of a region (the sensor region) of the sample and the reference waveguides. The polymeric transducer should be inert, that is, it must not interact chemically with the reagents taking part in the chemical or biochemical reaction under study.

Suitable polymers for use in the method according to the present invention include oligo- and polypeptides of greater than 10 amino acid monomer units, proteins, nucleic acids, oligo- and polynucleotides of greater than 10 nucleotide monomer units, and poly-olefinic compounds.
Preferred polymers for use in the method of the invention may be selected from the group consisting of: trypsin, myoglobin, ribonuclease A, fibrin, poly-L-glutamate, poly-α-benzyl-L-glutamate, salmon DNA, sea urchin DNA, polyadenylic acid (double-stranded), poly adenylic acid (single-stranded), polyadenylic acid-polyuridylic acid, polymethacrylic acid, poly-methyl methacrylate and polyallylamine.

Suitably, the optical waveguides are formed of a material that exhibits a refractive index to the electromagnetic radiation that will pass through the waveguide. The design and fabrication of a suitable optical waveguide will be well known to the skilled person. See, for example, Heideman and Lambeck, Proc. IEEE/LEOS Symp. (1997), pp 29–32. Suitable materials for forming the waveguide are disclosed in U.S. Pat. No. 5,465,151. Suitable polymeric materials for forming the optical waveguide are disclosed in WO 01/06240 (Gharavi, A.), for example, polyimide-alkoxy sulphone diazo stilbene, polyimide-dialkylamino nitro azo and polyimide-dialkyl amino diazo. Examples of other materials that may be used for fabricating optical waveguides include, but are not limited to, silicon oxide, silicon nitride, gallium arsenide, as well as glass and other siliceous materials. Particularly preferred materials are selected from silicon oxide and silicon nitride.

The electromagnetic radiation that is transmitted through the waveguide is suitably light radiation in the visible to near-infra-red region, preferably in the visible region from 400 nm to 1000 nm. The visible light is suitably supplied by a laser or a laser diode source, for example a VCSEL at 850 nm or helium neon laser at 632.8 nm.

Suitably, the said one or more components of said reaction are components of a chemical or biochemical reaction. In principle, any chemical or biochemical reaction may be studied using the apparatus and method according to the present invention. Examples of reactions that may be studied include, but are not limited to, enzyme assays, immunoassays, hydridization assays (for example DNA/DNA, RNA/RNA, RNA/DNA), protein/nucleic acid interactions and protein/protein binding assays. The apparatus and method is suitable for the measurement of the heat generated or taken up in any chemical reaction (in which $\Delta H \neq 0$), for example catalytic conversions, adduct addition and cellular biochemical processes in which changes in the metabolic status of an organism may be accompanied by changes in the heat output from the organism.

In order to clarify the principle and the function of the invention, reference is now made to the accompanying drawings in which.

Figure 1:
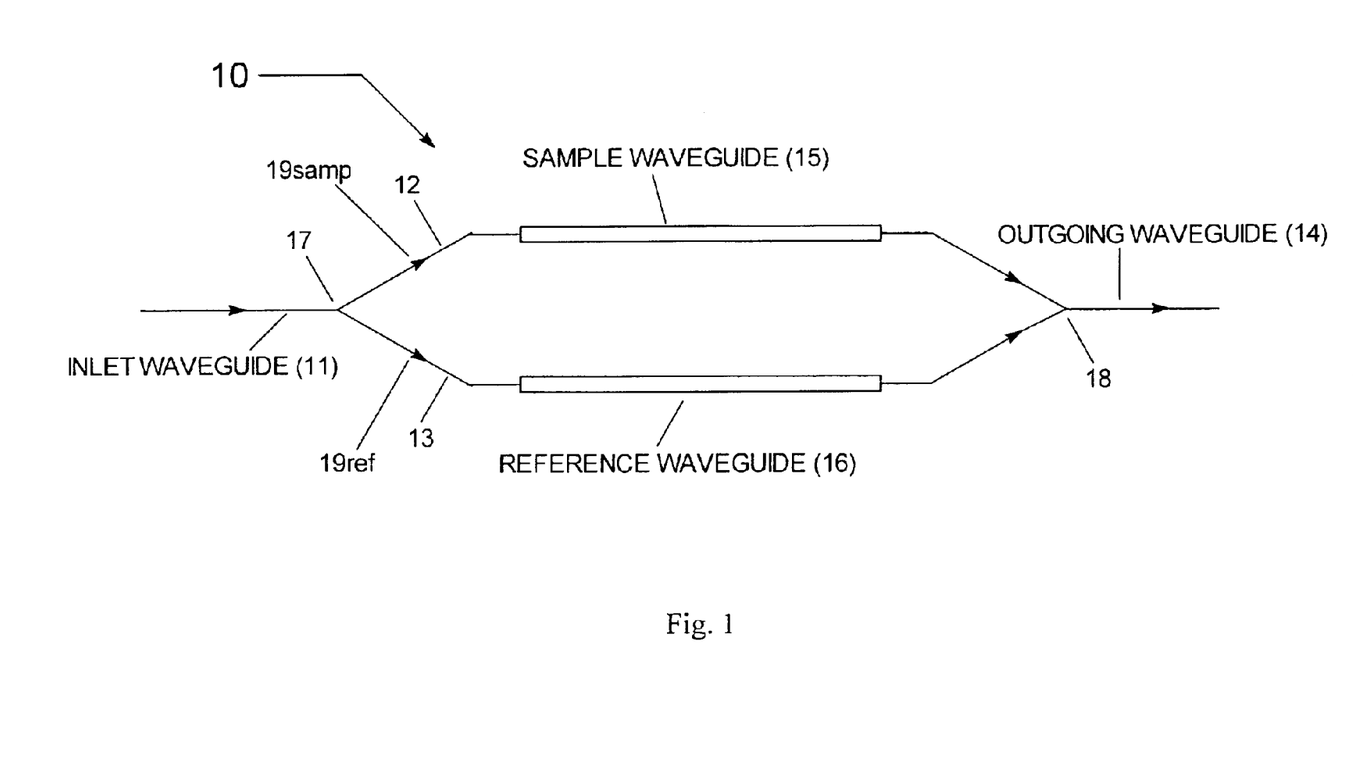
FIG. 1 shows a plan view of the optical system according to the invention and is based on a Mach-Zehnder interferometer.

Referring to FIG. 1, a Mach-Zehnder interferometer (10) is shown and is constructed having an inlet waveguide (11), an outgoing waveguide (14), a first channel (12) comprising a sample waveguide (15) and a second channel (13) comprising a reference waveguide (16). The two channels (12, 13) are joined in parallel at a first junction (17) to one end of the inlet wave-guide (11), and at a second junction (18) to one end of the outgoing waveguide (14). A beam (19) of electromagnetic radiation enters the inlet waveguide (11) and is guided down the inlet waveguide toward the first junction (17). At the first junction (17), the waveguide splits the beam (19) into both channels so as to allow a reference portion of the beam (19*ref*) to be transmitted into the reference waveguide (16) and a sample portion (19*samp*) to be transmitted into the sample waveguide (15). After passing through the reference and sample waveguides, the beams (19*ref*, 19*samp*) are reunited at the second junction (18) and exit through the outgoing waveguide (14). Any difference in the interference patterns between the first channel and the second channel will generate interference in the outgoing waveguide (14) that will be detected as a change in the transmitted intensity of the electromagnetic radiation.

The external surface of the sample waveguide and the reference waveguide are each suitably equipped with a sensor region which comprises a coating of a transducer material that is responsive to changes in heat in the reaction (either exothermic or endothermic) under study. Suitably, the transducer is a polymer layer, preferably an organic polymer or a biological macromolecule. It is known that biological macromolecules undergo a conformation change when they are subjected to a temperature change. Such conformational changes are accompanied by corresponding changes in refractive index. When the polymer is formed as a layer bound to the external surface of the sample waveguide and the reference waveguide, any change in the refractive index of the polymer will affect the refractive index of the sample and reference waveguide, thereby causing a change in the interference fringe pattern produced as a result.

Figure 2:
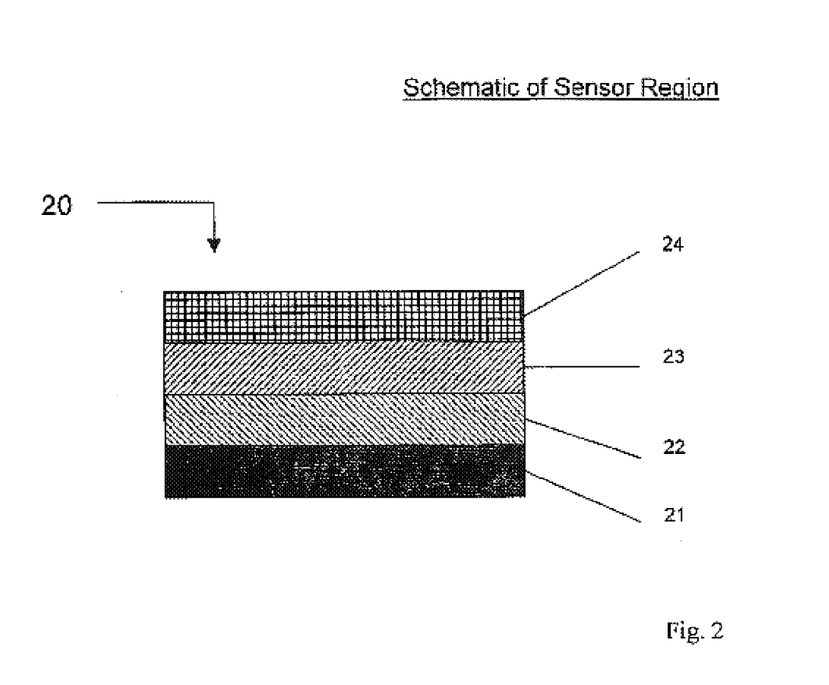
FIG. 2 is a schematic diagram showing, in cross-section, the sensor region of the apparatus according to the present invention.

FIG. 2 is a schematic diagram showing, in cross-section, the sensor region (20) of the apparatus according to the present invention. An optical waveguide system is known. See for example, the system described in WO 98/58285 (Heideman et al), which comprises a light guiding layer supported by a carrier support (21), preferably composed of $SiO_2$ having a thickness of about 500 nm. The light guiding layer comprises layers of $Si_3N_4$ (passive light guiding layer (22) and having a thickness, for example, of about 20 nm) and ZnO (electro-optical light guiding layer (23) having a thickness of about 500 nm). A transducer layer (24) is attached to the light guiding layer.

Suitably, the transducer polymer will be coated as a layer to a depth of between 50 nm and 250 nm, preferably about 100 nm. The polymer will be coated as a layer on both the sample and reference waveguides of the MZI.

A number of methods have been described to couple polymers to silicon surfaces. Generally they may be divided into methods which involve passive absorption or covalent linkage. Thus, the polymer may be dissolved in an organic solvent and the required volume applied to the surface of the sensor. The solvent is then driven off either passively or actively and the resulting polymer layer is left on the sensor surface. Alternatively, covalent coupling methods can be used to couple the polymer to the surface of the sensor. For example, Halliwell, C. M. and Cass, A. E. G., Analytical Chemistry, (2001), 73(11), 2476–83) describe the coupling of nucleic acids to surfaces using (3-mercaptopropyl)-trimethoxysilane. The silanization of surfaces has been extensively reviewed in the literature, for example, Kallury et al, Analytical Chemistry, (1988), 60, 169–172; Leyden in Silanes, Surfaces and Interfaces, Gordon and Breach, New York, 1986.

In practice, the surface of the sensor is cleaned using, for example, pirhana acid or oxygen plasma. The surface may then be silanised by treatment with 0.1% 3-aminopropyl triethoxysilane in toluene for approximately 1 hour, followed by heating at 110° C. for 2 hours. Following this treatment, the amino-functionalised surface is activated by 1% cyanuric chloride and 1% tribenzylamine for 4 hours at room temperature. The surface is then washed with toluene and petroleum ether, and then dried. Solutions of polymer in aqueous buffers such as PBS can now be added and incubated for 1 hour at room temperature. The surface is washed with 0.01% Tween to remove unbound material, and then with water.

The sample may be brought into contact with the sensor region in various ways as shown schematically in FIGS. 3 to 6.

Figure 3:
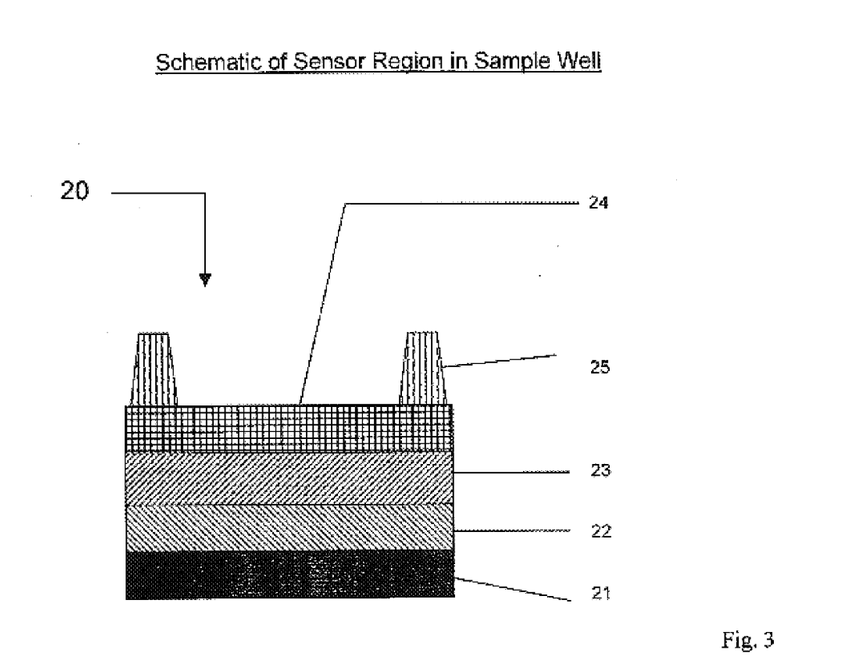
FIG. 3 is a schematic diagram showing, in cross section, a sample chamber for receiving a sample of a chemical or a biochemical reaction to be studied.

FIG. 3 shows a sample chamber for receiving a fluid sample of a chemical or a biochemical reaction to be studied. The sample chamber may be held in place over the sensor surface by mechanical means such as a clamp, or alternatively the sample well may be permanently attached to the sensor surface using adhesive. Suitably, the sample well (25) is of a one-piece moulded construction and may be formed from rigid materials, which are resistant to the aqueous, and/or aqueous/organic media used in the chemical or biochemical reactions under study. Suitable materials are selected from rigid plastic or polymeric materials. Alternatively, the reservoir may be formed by machining methods in the surface of a plastic or polymeric block. Preferred plastics are selected from polystyrene, polycarbonate, polypropylene, or poly-tetrafluoroethylene (PTFE; Teflon™).

Figure 4:
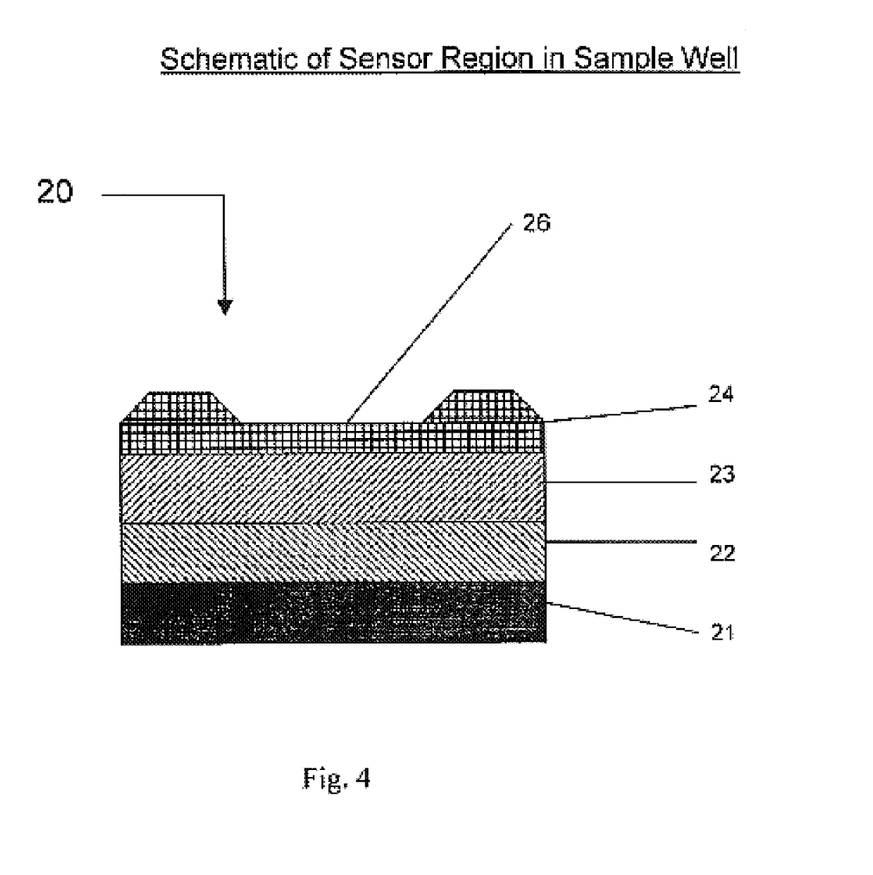
FIG. 4 is a schematic diagram illustrating, in cross section, an alternative sample chamber whereby channels or depressions are formed in the transducer layer to contain samples of reactants.

An alternative approach is to form the sample chamber into the surface of the transducer polymer layer, as shown in FIG. 4, as depressions (26) (or channels) to which samples of the chemical or biochemical reaction may be added directly.

Suitably, the sample chamber (25) and the depressions (26) for holding the reaction components may be of any cross-sectional shape, such as square, rectangular, circular, trapezoid and triangular and are sized to give a floor area between 100 $\mu m^2$ and 10,000 $\mu m^2$, preferably between 500 $\mu m^2$ and 1,000 $\mu m^2$. The plastic or polymer surface of the sample chamber may be selectively treated or modified to permit cell attachment and/or growth for the study of cellular reactions. Treatment preferably involves exposure to intense UV light to modify the polymer surface or alternatively the use of high voltage plasma discharge using known techniques (see Amstein, C. F. and Hartmann, P. A., J. Clin. Microbiol., (1975), 2(1), 46–54) to create a negatively charged surface suitable for cell growth and attachment. Cell attachment may be further improved by the application of additional coatings to the surface of the cell growth chamber, eg. polylysine, collagen, fibronectin.

Figure 5:
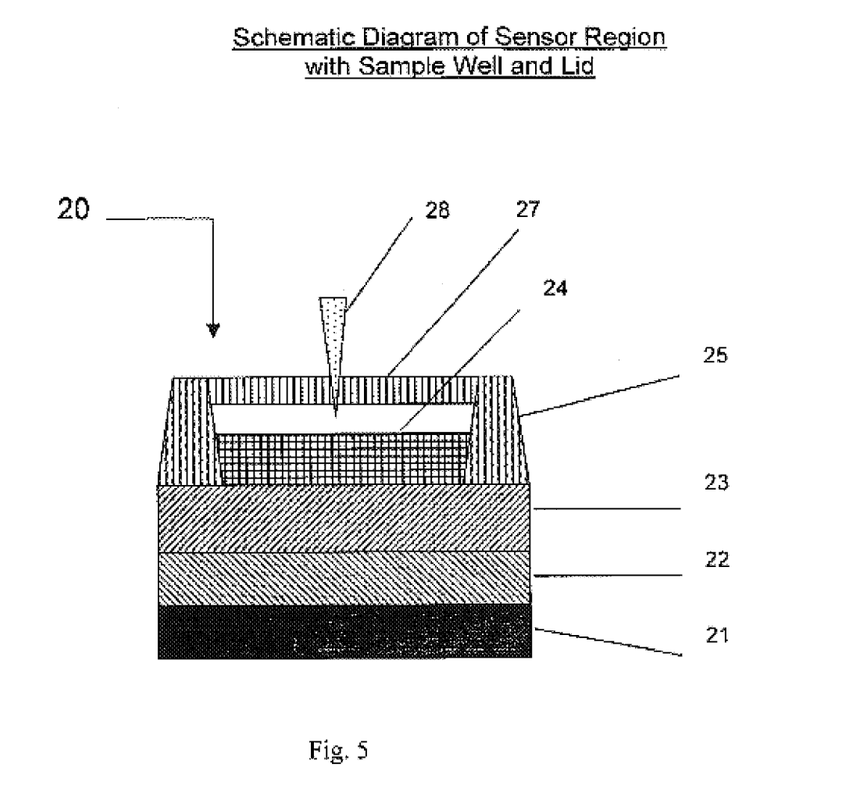
FIG. 5 is a schematic diagram showing, in cross section, a sample chamber provided with a cover or "lid" so as to insulate the chamber.

In a further embodiment, as shown in FIG. 5, the sample chamber (25) is provided with a cover or "lid" (27) so as to insulate the sensor surface from the environment, thereby minimising any loss of heat from the reaction under study. Samples may be introduced into the sample chamber and applied directly to the surface of the transducer polymer layer by injection, for example, by means of a syringe (28) through the lid (27). Furthermore, the lid (27) may be used to control the environment of the chamber by the passage of a coolant or heating fluid, such as water, through tubing (not shown) attached to a hollow lid.

Figure 6:
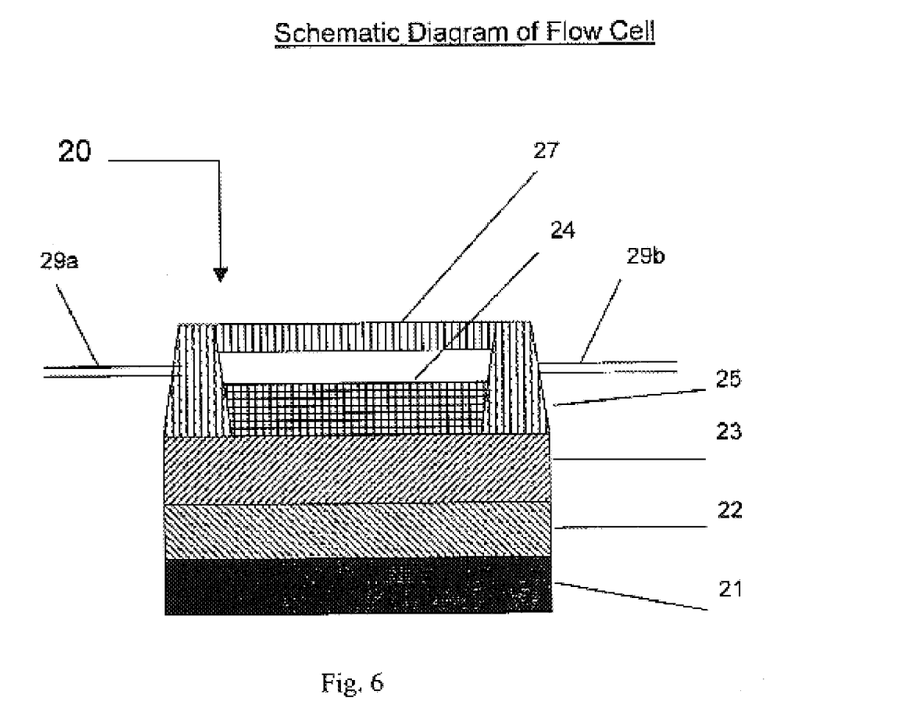
FIG. 6 is a schematic diagram shown in cross section, whereby the sensor surface is contained within a flow cell.

In a still further embodiment, the sensor surface is contained within a flow cell as shown in FIG. 6. A liquid sample containing components of the reaction to be studied enters the sample chamber by means of a reagent inlet pipe (29a) set into one side of the sample chamber. The sample leaves the sample chamber via an exit pipe (29b) set into the opposite side of the chamber. In use, reagents or wash solutions may be added to the sample chamber by pumping, for example, by means of a peristaltic pump or vacuum pump.

To perform a measurement of a change in the heat generated in a reaction, the components of the chemical or biochemical reaction to be studied (the reactants), typically in a reaction volume of 50–90 $\mu l$, are placed in contact with the sensor surface of the sample waveguide and the reference waveguide, without the initiator of the reaction being present. Laser light is allowed to pass through the waveguides and the fringe pattern, (ie. a series of spaced light bands), is recorded. The reactants are allowed to achieve thermal equilibrium, as judged by no change in the fringe pattern from the MZI. At this time, an initiator is added to the reactants in contact with the sample waveguide in a typical volume of 1–10 $\mu l$ and in a time of less than 0.1 sec. Any changes in the position of light bands of the fringe pattern are recorded continuously and the data stored by means of a computer.

For example, the enzyme β-lactamase may be assayed using the apparatus of FIG. 3 as follows:

i) prepare a 1 mM solution of penicillin G in PBS pH 7.0;

ii) add 50 µl of the 1 mM solution of Penicillin G to the sample wells located on both the sample and reference waveguides of the MZI;
iii) prepare a solution of the enzyme β-lactamase at 50 IU/10 µl in PBS pH 7.0;
iv) place 10 µl of the enzyme β-lactamase at 50 IU/10 µl in PBS pH 7.0 in the initiator addition device, such as a syringe;
v) record the fringe pattern from the MZI until a stable reading is obtained, continue to record this reading for 1 minute;
vi) add the enzyme to the penicillin solution in the sample well and simultaneously add 10 ul of buffer to the reference well in less than 0.1 seconds;
vii) record the fringe pattern for a period of 10 minutes;
viii) determine the rate of change of the fringe as fringes/second;
ix) repeat steps i) to viii) using a range of concentrations of Penicillin G;
x) using the data from step viii), plot the rate of change of the fringes (as fringes per second) versus the concentration penicillin G to obtain data for the kinetic properties of the enzyme such as $V_{max}$ and $K_m$ without the need for absolute knowledge of the temperature or $\Delta G$ involved in the reaction.

The correlation of changes in the fringe pattern of the MZI to energy changes in the chemical or biochemical reaction may be accomplished in a number of ways.

1. A platinum resistor may be placed within the sample chamber in the presence of a suitable quantity of water. Electric current may be passed through the resistor so that the amount of energy dissipated may be readily calculated. The resultant changes in the position of light bands in the fringe pattern may then be related to the energy passed through the resistor and the energy so received. This process may be repeated for a number of different current settings.
2. In an alternative and preferred method, the energy released from a chemical or biochemical reaction may be used. For example, Wadso, (Thermochemica Acta, (2000), 347, 73–77) describes the use of a number of chemical reactions which generate well-defined amounts of heat. This could include the aqueous dissolution of propan-1-ol.

Advantages of the Present Invention i) The method of the invention may be used with sample volumes of 100 µl or less.
ii) The surface of the transducer polymer layer is non-functionalised and the method according to the present invention does not rely on specific binding of reactants to the surface of the waveguide. The apparatus may therefore be used for the measurement of heat generated with different reaction types.
iii) Many prior art calorimeters use direct detection of heat change, which is typically measured via a change in the signal from a metal or semi-conductor device and is related to the Seebeck coefficient of the material being used. The Seebeck coefficient of materials limits the sensitivity of such devices to about $10^{-4}$ to $10^{-5}$° C. and therefore requires relatively large sample volumes, typically greater than 1 ml. The present invention utilises an indirect optical detection system which is not limited by the Seebeck coefficient. The sensitivity will be of the order of $10^{-6}$ degrees change in temperature.

iv) The apparatus and method according to the invention may be used in real time measurements of heats of chemical or biochemical reactions. When a difference appears between the sample and reference arms of the MZI, this difference will be reported instantaneously.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. In a method for detecting a heat change in a reaction wherein said heat change is detected by using an interferometric detection system which includes an inlet waveguide, a sample waveguide, a reference waveguide, and an outgoing waveguide;

the improvement comprising selecting said sample and reference waveguides formed of a material having an index of refraction, said sample and reference waveguides being joined at a first junction to said inlet waveguide and at a second junction to the outgoing waveguide such that electromagnetic radiation is allowed to pass simultaneously in parallel through said sample and reference waveguides;

and further each of said sample waveguide and said reference waveguide includes a surface that is coated with a transducer responsive to a heat change in a reaction and is bound thereto.

2. The method of claim 1 wherein:
i) the surfaces of said waveguides are contacted with a liquid including one or more components of said reaction to be studied;
ii) a beam of electromagnetic radiation is directed through said waveguides in the absence and in the presence of an initiator of said reaction added to said sample waveguide thereby producing a fringe pattern including a plurality of spaced light bands whose positions shift in response to changes in the heat of said reaction;
wherein the positional shifts of said light bands in said fringe pattern measured in the absence and in the presence of said initiator are used to calculate the heat change in said reaction.

3. The method of claim 1 wherein said transducer is an organic polymer or biological macromolecule.

4. The method of claim 3 wherein said organic polymer or biological macromolecule and is selected from the group consisting of: trypsin, myoglobin, ribonuclease A, fibrin, poly-L-glutamate, poly-α-benzyl-L-glutamate, salmon DNA, sea urchin DNA, polyadenylic acid (double-stranded), poly adenylic acid (single-stranded), polyadenylic acid-polyuridylic acid, poly-methacrylic acid, poly-methyl methacrylate and poly-allylamine.

5. The method of claim 1 wherein said surface is coated with the transducer to a thickness of between 50 nm and 250 nm.

6. A system for detecting the heat change in a reaction comprising
i) an inlet waveguide;
ii) a sample waveguide;
iii) a reference waveguide; and
iv) an outgoing waveguide
wherein the improvement comprising selecting said sample and reference waveguides formed of a material having an index of refraction, said sample and reference waveguides being joined at a first junction to said inlet waveguide and at a second junction to the outgoing waveguide such that electromagnetic radiation is allowed to pass simultaneously in parallel through said sample and reference waveguides; and further each of said sample waveguide and said reference waveguide includes a surface that is coated with a transducer responsive to a heat change in a reaction and is bound thereto.

7. The system of claim 6 wherein:
 i) the surfaces of said waveguides are contacted with a liquid including one or more components of said reaction to be studied;
 ii) a beam of electromagnetic radiation is directed through said waveguides in the absence and in the presence of an initiator of said reaction added to said sample waveguide thereby producing a fringe pattern including a plurality of spaced light bands whose positions shift in response to changes in the heat of said reaction; wherein the positional shifts of said light bands in said fringe pattern measured in the absence and in the presence of said initiator are used to calculate the heat change in said reaction.

8. The system of claim 6 wherein said transducer is an organic polymer or biological macromolecule.

9. The system of claim 8 wherein said organic polymer or biological macromolecule and is selected from the group consisting of: trypsin, myoglobin, ribonuclease A, fibrin, poly-L-glutamate, poly-α-benzyl-L-glutamate, salmon DNA, sea urchin DNA, polyadenylic acid (double-stranded), poly adenylic acid (single-stranded), polyadenylic acid-polyuridylic acid, poly-methacrylic acid, poly-methyl methacrylate and poly-allylamine.

10. The system of claim 6 wherein said surface is coated with the transducer to a thickness of between 50 nm and 250 nm.

* * * * *